US006726723B2

(12) United States Patent
Running

(10) Patent No.: US 6,726,723 B2
(45) Date of Patent: *Apr. 27, 2004

(54) POSTERIOR STABILIZED MOBILE BEARING KNEE

(75) Inventor: Donald E. Running, Warsaw, IN (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/230,529

(22) Filed: Aug. 29, 2002

(65) Prior Publication Data

US 2003/0004577 A1 Jan. 2, 2003

Related U.S. Application Data

(63) Continuation of application No. 09/395,584, filed on Sep. 14, 1999, now Pat. No. 6,443,991.
(60) Provisional application No. 60/127,929, filed on Apr. 6, 1999, and provisional application No. 60/101,312, filed on Sep. 21, 1998.

(51) Int. Cl.[7] .................................................. A61F 2/38
(52) U.S. Cl. .................................. 623/20.27; 623/20.29
(58) Field of Search .......................... 623/20.14–20.15, 623/20.21, 20.23–20.29, 20.31–20.35, 23.39, 23.41; 606/60

(56) References Cited

U.S. PATENT DOCUMENTS

| 3,728,742 | A | 4/1973 | Averill et al. |
| 3,748,662 | A | 7/1973 | Helfet |
| 3,774,244 | A | 11/1973 | Walker |

(List continued on next page.)

FOREIGN PATENT DOCUMENTS

| EP | 0 346 183 | 5/1989 |
| EP | 0 627 203 A2 | 12/1994 |
| EP | 0 838 204 A2 | 4/1998 |
| WO | WO 98/25550 | 6/1998 |
| WO | WO 99/30649 | 6/1999 |

OTHER PUBLICATIONS

P.F.C.® Sigma Knee System Brochure (one page, printed on both sides), Johnson & Johnson Orthopaedics, Inc., ©1998.

Six (6) sheets of technical drawings of various prosthetic knee components which may have been publicly used at least as early as Sep. 20, 1997.

Primary Examiner—David H. Willse
Assistant Examiner—Urmi Chattopadhyay
(74) Attorney, Agent, or Firm—Maginot, Moore & Beck

(57) ABSTRACT

A knee prosthesis and method for use are provided, in which the knee prosthesis provides anterior and posterior stability and controlled femoral roll-back, while also providing rotational kinematics. The femoral component has a pair of convexly shaped condyles which are spaced apart to form an intercondylar notch. Anterior and posterior cams are provided within the notch. The tibial component comprises a platform upon which a tibial bearing is mounted to provide for rotational movement about the tibial axis. The tibial bearing is provided with surfaces to engage the condyles and has an upwardly extending spine which is positioned to engage the anterior and posterior femoral cams. At full extension, the spine engages the anterior femoral cam to provide a 3° hyperextension stop. Between full extension and approximately 50° of flexion, the spine is free to translate between the anterior and posterior femoral cams. From 50° to 120° of flexion, the spine engages the posterior femoral cam, which provides femoral roll-back and posterior stability.

9 Claims, 4 Drawing Sheets

U.S. PATENT DOCUMENTS

| | | |
|---|---|---|
| 3,840,905 A | 10/1974 | Deane |
| 3,869,729 A | 3/1975 | Attenborough |
| 3,964,106 A | 6/1976 | Hutter, Jr. et al. |
| 3,996,624 A | 12/1976 | Noiles |
| 4,016,606 A | 4/1977 | Murray et al. |
| 4,041,550 A | 8/1977 | Frazier |
| 4,064,568 A | 12/1977 | Grundei et al. |
| 4,081,866 A | 4/1978 | Upshaw et al. |
| 4,085,466 A | 4/1978 | Goodfellow et al. |
| 4,094,017 A | 6/1978 | Matthews et al. |
| 4,136,405 A | 1/1979 | Pastrick et al. |
| 4,167,047 A | 9/1979 | Grundei et al. |
| 4,207,627 A | 6/1980 | Cloutier |
| 4,209,861 A | 7/1980 | Walker et al. |
| 4,213,209 A | 7/1980 | Insall et al. |
| 4,216,549 A | 8/1980 | Hillberry et al. |
| 4,219,893 A | 9/1980 | Noiles |
| 4,224,696 A | 9/1980 | Murray et al. |
| 4,224,697 A | 9/1980 | Murray et al. |
| 4,249,270 A | 2/1981 | Bahler et al. |
| 4,262,368 A | 4/1981 | Lacey |
| 4,298,992 A | 11/1981 | Burstein et al. |
| 4,301,553 A | 11/1981 | Noiles |
| 4,309,778 A | 1/1982 | Buechel et al. |
| 4,340,978 A | 7/1982 | Buechel et al. |
| 4,353,135 A | 10/1982 | Forte et al. |
| 4,358,859 A | 11/1982 | Schurman et al. |
| 4,470,158 A | 9/1984 | Pappas et al. |
| 4,501,031 A | 2/1985 | McDaniel et al. |
| 4,502,161 A | 3/1985 | Wall |
| 4,538,305 A | 9/1985 | Engelbrecht et al. |
| 4,568,348 A | 2/1986 | Johnson et al. |
| 4,586,933 A | 5/1986 | Shoji et al. |
| 4,634,444 A | 1/1987 | Noiles |
| 4,714,474 A | 12/1987 | Brooks, Jr. et al. |
| 4,728,332 A | 3/1988 | Albrektsson |
| 4,770,663 A | 9/1988 | Hanslik et al. |
| 4,790,853 A | 12/1988 | Engelbrecht et al. |
| 4,795,468 A | 1/1989 | Hodorek et al. |
| 4,822,366 A | 4/1989 | Bolesky |
| 4,865,606 A | 9/1989 | Rehder |
| 4,888,021 A | 12/1989 | Forte et al. |
| 4,892,547 A | 1/1990 | Brown |
| 4,944,757 A | 7/1990 | Martinez et al. |
| 4,950,297 A | 8/1990 | Elloy et al. |
| 4,950,298 A | 8/1990 | Gustilo et al. |
| 4,959,071 A | 9/1990 | Brown et al. |
| 5,007,933 A | 4/1991 | Sidebotham et al. |
| 5,011,496 A | 4/1991 | Forte et al. |
| 5,019,103 A | 5/1991 | Van Zile et al. |
| 5,061,271 A | 10/1991 | Van Zile |
| 5,071,438 A | 12/1991 | Jones et al. |
| 5,116,375 A | 5/1992 | Hofmann |
| 5,116,376 A | 5/1992 | May |
| 5,123,928 A | 6/1992 | Moser |
| 5,147,405 A | 9/1992 | Van Zile et al. |
| 5,171,283 A | 12/1992 | Pappas et al. |
| 5,194,066 A | 3/1993 | Van Zile |
| 5,236,461 A | 8/1993 | Forte |
| 5,246,459 A | 9/1993 | Elias |
| 5,271,747 A | 12/1993 | Wagner et al. |
| 5,282,866 A | 2/1994 | Cohen et al. |
| 5,290,313 A | 3/1994 | Heldreth |
| 5,314,481 A | 5/1994 | Bianco |
| 5,326,361 A | 7/1994 | Hollister |
| 5,330,532 A | 7/1994 | Ranawat |
| 5,330,534 A | 7/1994 | Herrington et al. |
| 5,356,414 A | 10/1994 | Cohen et al. |
| 5,358,527 A | 10/1994 | Forte |
| 5,358,530 A | 10/1994 | Hodorek |
| 5,370,699 A | 12/1994 | Hood et al. |
| 5,370,701 A | 12/1994 | Finn |
| 5,387,240 A | 2/1995 | Pottenger et al. |
| 5,395,401 A | 3/1995 | Bahler |
| 5,405,398 A | 4/1995 | Buford, III et al. |
| 5,411,555 A | 5/1995 | Nieder |
| 5,413,608 A | 5/1995 | Keller |
| 5,489,311 A | 2/1996 | Cipolletti |
| 5,514,183 A | 5/1996 | Epstein et al. |
| 5,549,686 A | 8/1996 | Johnson et al. |
| 5,549,687 A | 8/1996 | Coates et al. |
| 5,549,689 A | 8/1996 | Epstein et al. |
| 5,609,639 A | 3/1997 | Walker |
| 5,609,642 A | 3/1997 | Johnson et al. |
| 5,609,645 A | 3/1997 | Vinciguerra |
| 5,613,970 A | 3/1997 | Houston et al. |
| 5,634,927 A | 6/1997 | Houston et al. |
| 5,639,279 A | 6/1997 | Burkinshaw et al. |
| 5,658,341 A | 8/1997 | Delfosse |
| 5,658,342 A | 8/1997 | Draganich et al. |
| 5,658,344 A | 8/1997 | Hurlburt |
| 5,683,467 A | 11/1997 | Pappas |
| 5,683,469 A | 11/1997 | Johnson et al. |
| 5,683,470 A | 11/1997 | Johnson et al. |
| 5,702,458 A | 12/1997 | Burstein et al. |
| 5,702,466 A | 12/1997 | Pappas et al. |
| 5,755,801 A | 5/1998 | Walker et al. |
| 5,755,804 A | 5/1998 | Schmotzer et al. |
| 5,766,257 A | 6/1998 | Goodman et al. |
| 5,776,201 A | 7/1998 | Colleran et al. |
| 5,800,552 A | 9/1998 | Forte |
| 6,123,729 A | 9/2000 | Insall et al. |
| 6,443,991 B1 * | 9/2002 | Running ............... 623/20.27 |

\* cited by examiner

POSTERIOR STABILIZED MOBILE BEARING KNEE

CROSS-REFERENCE

This application is a continuation of U.S. patent application Ser. No. 09/395,584, filed on Sep. 14, 1999, now U.S. Pat. No. 6,443,991, which in turn claims the benefit of both (i) U.S. Provisional Patent Application Ser. No. 60/127,929, filed on Apr. 6, 1999, and (ii) U.S. Provisional Patent Application Ser. No. 60/101,312, filed Sep. 21, 1998, the disclosures of each of these three patent applications are hereby incorporated by reference for all purposes in their entirety.

BACKGROUND AND SUMMARY OF THE INVENTION

The present invention relates to a knee prosthesis and more particularly to the provision of a knee prosthesis comprising a rotating bearing on the tibial platform with a spine for posterior stabilization of the anterior-posterior translation of the femoral component relative to the tibial component.

The prior art includes various examples of knee prostheses. Examples of posterior stabilized knee prostheses can be found in U.S. Pat. Nos. 4,298,992 and 5,147,405. Also, examples of knee prostheses which provide a rotational bearing can be found in U.S. Pat. Nos. 4,470,158 and 5,395,401. These references are incorporated herein by reference.

The present invention provides a knee prosthesis comprising a femoral component adapted to be implanted on the condylar portions of the femur and having a pair of laterally spaced-apart condylar portions, each of which has an external surface that is preferably smoothly convexly curved in the antero-posterior direction and generally matches the shapes in lateral profile of condylar surfaces of the femur. These condylar surfaces are preferably smoothly convexly curved in all cross-sections along their antero-posterior extent, and the intercondylar portion connecting the condylar portions defines an intercondylar notch having spaced-apart lateral surfaces or walls. This intercondylar notch may preferably be a box-like housing having spaced-apart lateral side walls and an open roof. Within this notch, the femoral component preferably provides an anterior femoral cam and a posterior femoral cam. The prosthesis further comprises a tibial component adapted to be implanted on the tibial platform and including a bearing having on its superior surface a pair of laterally spaced-apart concavities or bearing surfaces, each of which is adapted to receive in nested relation one of the condylar portions of the femoral component. This bearing is preferably formed to include a superior extending spine to be received in the intercondylar notch of the femoral component. The spine preferably has lateral surfaces, an anterior tibial cam, and a posterior tibial cam. A platform is provided to be rigidly attached to the proximal end of the tibia to provide a surface upon which the bearing rotates about an axis generally aligned with the tibia.

In the illustrated embodiment, the relative positions and shapes of the spine and the intercondylar notch of the prosthesis as implanted into the knee joint are such that, when the leg is at or near full extension, where the femur tends to dislocate posteriorly relative to the tibia, the anterior femoral and tibial cams engage each other to prevent posterior dislocation of the femoral component. When the leg is partly flexed, the femoral and tibial cams are spaced-apart from each other and permit relatively free antero-posterior translation of the components but are available to restrain excessive anterior and posterior movements. From approximately 40° to 60° of flexion to approximately 120° of flexion, the posterior femoral and tibial cams engage and bear on each other. Preferably, the posterior cams engage from approximately 50° to approximately 120° of flexion. During this flexion, the tibial cam prevents the femoral component from moving anteriorly, and the tibio-femoral contact shifts posteriorly. This femoral roll-back theoretically provides for increased range of motion and improved quadriceps efficiency at deeper flexion angles. Further, preferably, the relative positions and shapes of the posterior femoral and tibial cams of the prosthesis as implanted in the knee joint are such that, when the leg approaches full flexion, the tibial cam is of sufficient height to prevent anterior dislocation of the femoral component.

The present invention also provides a method for controlling the antero-posterior translation of a knee prosthesis comprising the steps of providing a femoral component and attaching the femoral component to a femur at its distal end. The femoral component has condyle surfaces which are spaced apart to define a notch therebetween and a femoral anterior cam and a femoral posterior cam disposed in the notch. A tibial component is provided to be attached to the tibia at its proximal end and the tibial component comprises a platform to be attached to the tibia and a bearing mounted on the platform for rotational movement about an axis extending generally in the direction of the tibia. In the method of the present invention, the bearing is formed to provide bearing surfaces for movably supporting the femoral component condyle surfaces. The bearing is also provided with a spine extending superiorly (upwardly) into the notch between the condyle surfaces. This spine is provided for engaging the femoral anterior posterior cams to provide anterior and posterior stability and femoral roll-back. Also, the spine is of sufficient size to provide an adequate subluxation height. The tibial anterior cam preferably inclines upwardly from the anterior portion of the bearing, and the tibial posterior cam preferably inclines downwardly from the peak at a point adjacent the axis of rotation of the bearing and generally parallel to the rotational axis.

The illustrative tibial anterior cam surface inclines upward slightly from the anterior most portion of the bearing to a point at which the inclination is about 40° to 50° up to the peak of the spine. The illustrative femoral anterior cam is convexly curved to have a curve portion generally aligned with the more inclined portion of the tibial anterior cam from said point to the peak when the knee is at full extension. The femoral posterior cam is also convexly curved, and it is placed to engage the tibial posterior cam when the knee is at about 40° to 60° of flexion, preferably at about 50° of flexion. At that point, the tibial posterior cam prevents the femoral component from further anterior translation. From 40° to 60° of flexion to 120° of flexion, the femoral posterior cam continues to engage the tibial posterior cam, and roll-back occurs during such flexion. Preferably, a spine is provided of sufficient height to reduce the possibility of dislocation from approximately 90° to 120° of flexion.

DETAILED DESCRIPTION OF THE DRAWINGS

Figure 1:
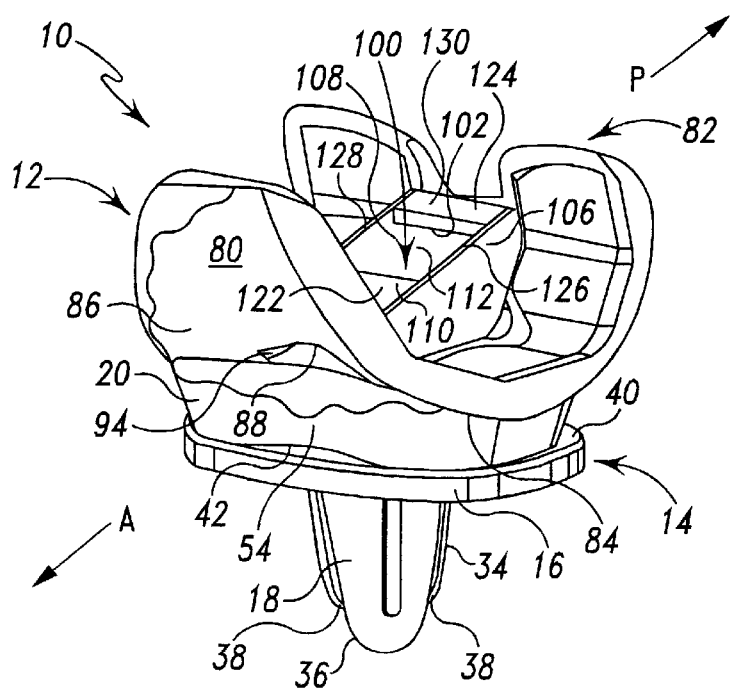
FIG. 1 is a perspective view of the knee system of the present invention showing the femoral component and the tibial component with the tibial bearing.
Figure 2:
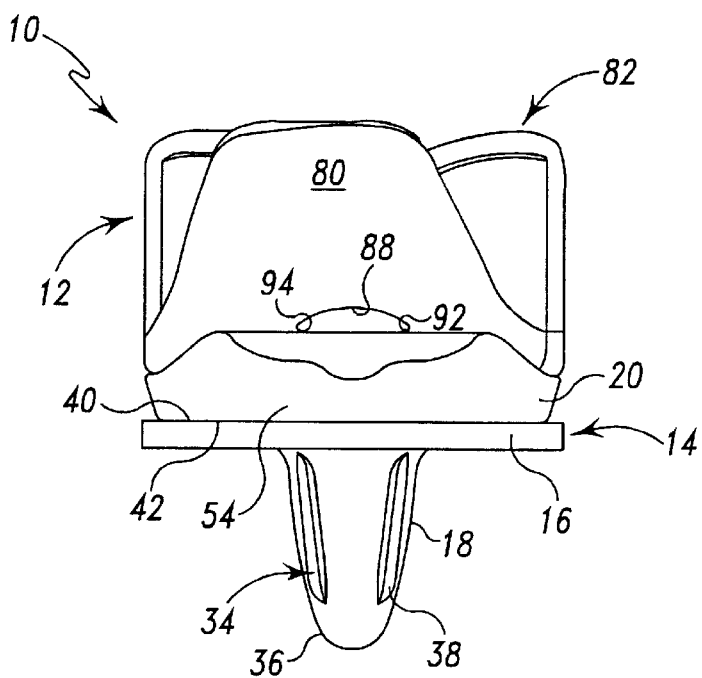
FIG. 2 is an elevation view from the anterior of FIG. 1.
Figure 3:
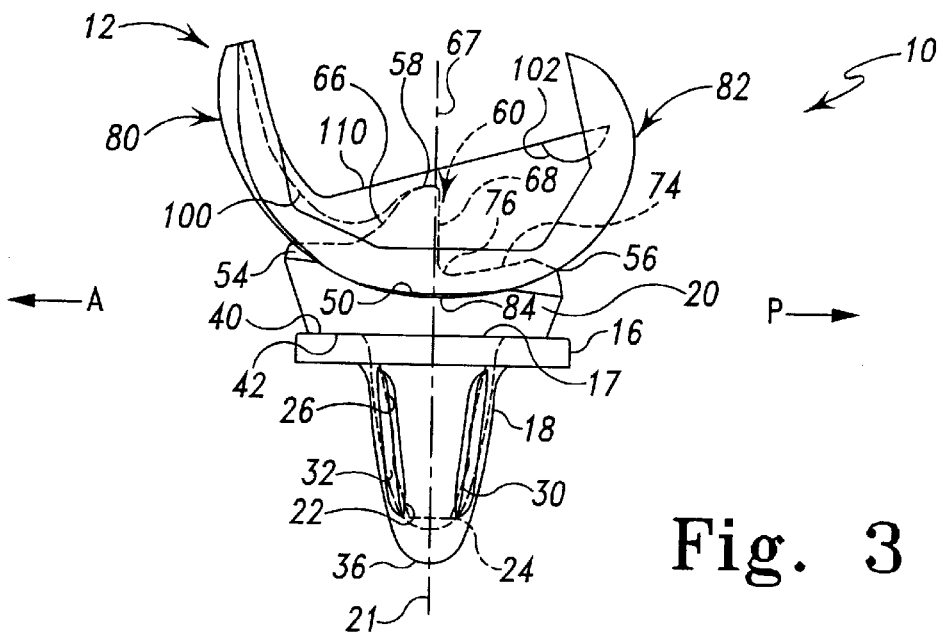
FIG. 3 is a side view of the assembly shown in FIGS. 1 and 2.
Figure 4:
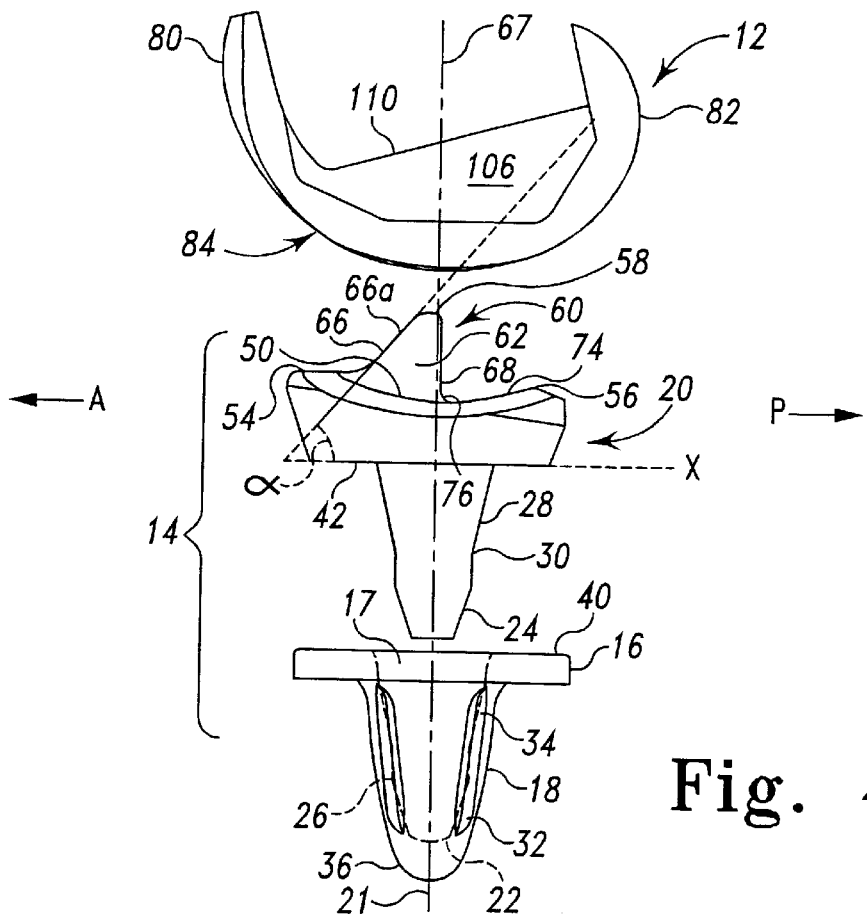
FIG. 4 is an exploded side view showing the plastic bearing element removed from the tibial platform.

Referring specifically to FIG. 1, it will be seen that a knee system 10 of the present invention comprises a femoral component 12 and a tibial component 14. The tibial component 14 comprises a tibial platform 16 from which a tibial stem 18 extends downwardly, and a bearing 20 which mounts on platform 16. As indicated in FIGS. 3 and 4, the tibial platform 16 is provided with a socket 26 extending downwardly from an opening 17 in the platform, for receiving a stem 28 which extends downwardly from the bearing 20. Also as shown in FIGS. 3 and 4, the stem 28 of bearing 20 is provided with a generally cylindrical portion 30, which rotatably seats in a generally cylindrical portion 32 of socket 26, and stem 28 terminates in a distal tapered portion 24, which seats in a mating distal tapered portion 22 of socket 26. However, it will be understood that stem 28 and socket 26 need not be provided with such cylindrical and tapered portions. Other mounting configurations which allow for relatively free rotational movement are within the scope of this invention.

As best seen in FIG. 1, the illustrative tibial stem 18 is provided with radially spaced-apart, downwardly extending ridges 34 which extend toward a distal tip 36 of the stem and which terminate as indicated at 38. These radially spaced-apart ridges 34 serve to anchor the tibial component 14 in the tibia against rotation about the axis of the stem 18. It is well known that the stem 18 may be provided with a porous metal coating into which the bone of the tibia will grow to hold the tibial component in position in the tibia. It is also well known that the tibial component 14 may be cemented within the tibia. Other configurations and techniques for anchoring tibial component 14 to a tibia are known and are within the scope of this invention. The tibial platform 16 provides an upper platform surface 40 which serves as a bearing surface to support a bottom surface 42 of the bearing 20. The bearing 20 is permitted to rotate about the axis 21 (see FIGS. 3 and 4) of its stem 28 which is received in the socket 26. Such bearings are known as rotary bearings in that the bearing 20 can move rotationally relative to the tibial platform 16 which is anchored to the tibia.

Figure 6:
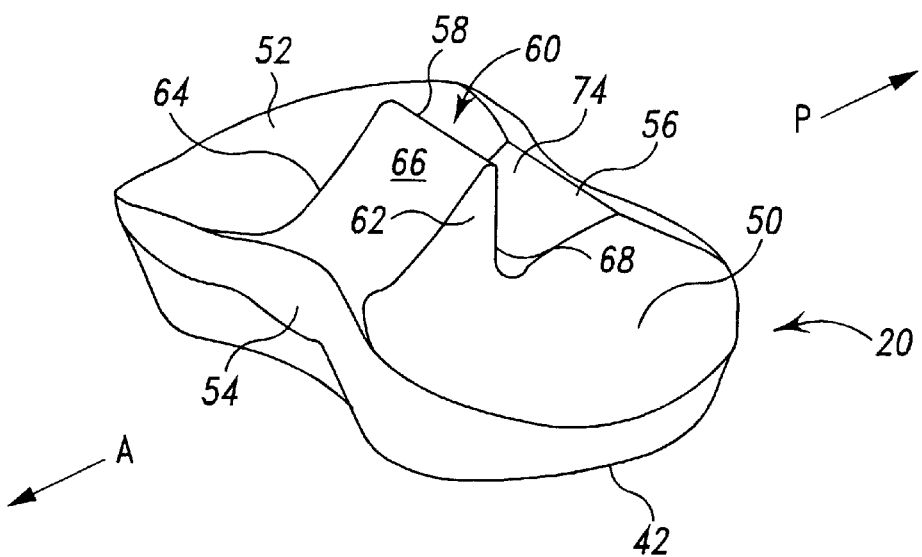
FIG. 6 is a perspective view of the upper portion of the bearing component.
Figure 7:
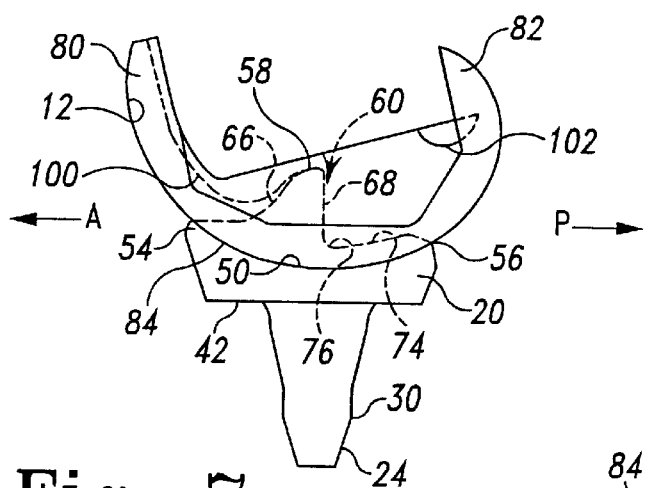
FIG. 7 is a diagrammatical side view showing the knee at full extension.

Referring to FIG. 6, the perspective view of the upper portion of the bearing 20, it will be seen that the bearing 20 is provided with bearing surfaces 50, 52 for supporting condyle bearings 84, 86 of the femoral component 12. Bearing surfaces 50, 52 may be configured in a number of manners, such as those disclosed in U.S. Pat. Nos. 4,309,778, 4,340,978, and 4,470,158, which are hereby incorporated by reference. A spine 60, sometimes referred to as an eminence or post, is located between the bearing surfaces 50, 52 and is provided with sides 62, 64 extending upwardly. The spine 60 is also provided with an anterior tibial cam 66, a posterior tibial cam 68, and a peak 58 therebetween. A ramp 74 is located posteriorly of the spine 60 to incline upwardly to a posterior end 56, as best seen in FIG. 4. The posterior tibial cam 68 of the spine 60 and the ramp 74 join to provide a notch or smooth transition 76, also best seen in FIG. 4. Referring further to FIG. 4, it will be seen that the anterior tibial cam 66 is a ramp-like surface beginning near the anterior portion of the bearing 20 and ramping upwardly and rearwardly to the peak of the spine 60. Initially, near an anterior end 54 of the bearing 20, the anterior tibial cam 66 inclines slightly upwardly, and further back the anterior tibial cam 66 includes a surface 66a inclined at an angle $\alpha$ of about 40° to 50° relative to plane x. Plane x may be thought of as coincident with surface 42 of bearing 20 that contacts platform 16 or, alternatively, may be thought of as a plane generally perpendicular to the axis of stem 28. Alternatively, if the prosthesis is implanted in a patient whose leg is positioned at full extension as shown in FIG. 7 on a flat level surface, plane x may be thought of as parallel to that flat level surface. In the illustrative embodiment of FIG. 4, angle $\alpha$ is about 45°.

In the illustrative embodiment, posterior tibial cam 68 is essentially planar and extends essentially linearly in the proximal-distal direction from peak 58 to transition 76. In particular, as shown in the side elevational views of FIGS. 3 and 4, the posterior tibial cam 68 defines a vertically extending line 67 which is arranged to be coincident with, or otherwise coaxially arranged with, the rotary axis 67 of the bearing 20. However, posterior tibial cam 68 may be curved in any number of ways and still provide a suitable surface for providing roll-back and posterior stability. Such alternative spine configurations are within the scope and spirit of this invention.

Figure 5:
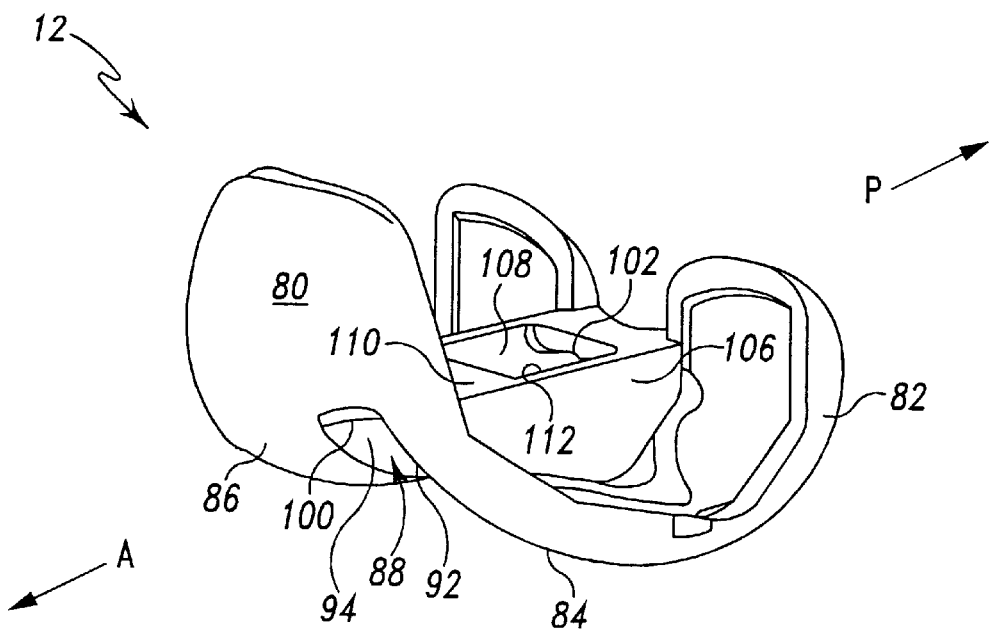
FIG. 5 is a perspective view of the femoral component.
Figure 8:
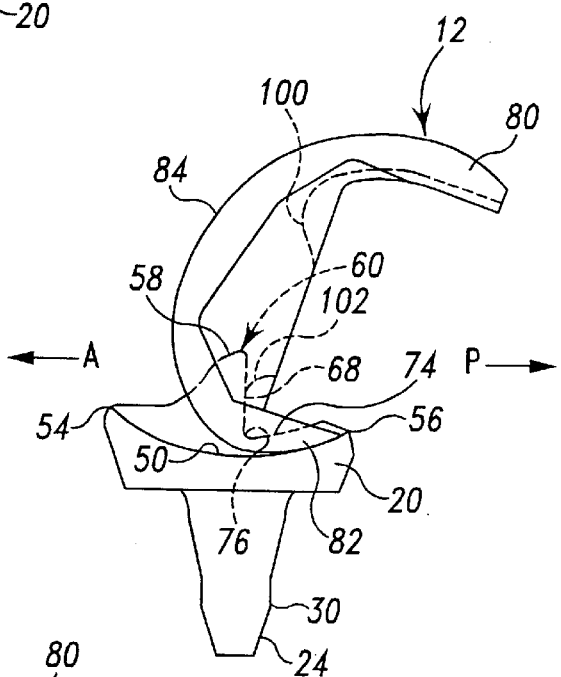
FIG. 8 is a diagrammatical side view showing the knee at 120° flexion.

As best seen in FIG. 5, the femoral component 12 is conventionally formed to have an anterior portion 80 and a posterior portion 82 providing condyles or condyle bearings 84, 86 for movably engaging bearing surfaces 50, 52 of the bearing 20. Preferred embodiments may be found in the '778 and '978 patents, which were discussed above and incorporated by reference. Conventionally, the femoral component 12 may be made from a suitable metal, while the bearing 20 may be made from a plastic material such as ultra high molecular weight polyethylene (UHMWPE). The prior art references referred to above describe the nature of the acceptable prosthesis implant metals and plastics. The condyle bearings 84, 86 will have radii of curvature to provide appropriate contact between the femoral component 12 and tibial component 14 as discussed in the prior art. It will be appreciated that, while at full extension as depicted in FIG. 7, the condyle bearings 84, 86 are more congruent with the bearing 20 surfaces 50, 52 than when the knee is at 120° of flexion, as depicted in FIG. 8. At 120° of flexion, only the posterior-most portion of the condyle bearings 84, 86 will be in contact with the bearing 20 surfaces 50, 52, and the contact point will be shifted posteriorly.

It will further be appreciated that in typical knee action, there is considerable anterior-posterior movement of the femoral component 12 on the tibial component 14, the anterior direction being represented by the arrow "A" and the posterior direction being represented by the arrow "P" in the drawings. According to this invention, this translation of the femoral component 12 relative to the tibial component 14 is controlled as the knee moves between full extension and full flexion. This control is provided by the spine 60 with its cams 66, 68. Specifically, the spine 60 extends upwardly into an intercondylar notch 88, which is located between condyle bearings 84, 86 in femoral component 12. Inside this intercondylar notch 88 is an anterior femoral cam 100 and a posterior femoral cam 102 for engaging, respectively, the anterior tibial cam 66 and posterior tibial cam 68 of the spine 60. This relationship is best seen in FIG. 3 and FIGS. 7–9. As best seen in FIG. 3, the anterior femoral cam 100 on femoral component 12 is convex and extends distally from the anterior portion of a roof 110 of the intercondylar notch 88, as best seen in FIG. 3 and in FIGS. 7–9. Likewise, the posterior femoral cam 102 on femoral component 12 is similarly convex and extends distally from the posterior part of roof 110 of the intercondylar notch 88.

As best seen in FIG. 5, interior walls 92, 94 of the intercondylar notch 88 are provided by a cam housing formed by sides 106, 108 and roof 110 which illustratively has a square aperture 112 formed therein. The femoral component 12 may be cemented to the resected femur or the femoral component may be coated with a porous material for bone ingrowth. Alternatively, a stem-like fastening component (not shown) may extend upwardly through aperture 112 to secure femoral component 12 to the femur. In a preferred embodiment, shown in FIG. 1, the flat roof may be omitted, and a proximal end 130 of the intercondylar notch 88 may be defined only by a proximal surface 122 of anterior femoral cam 100, a proximal surface 124 of posterior femoral cam 102, a proximal edge 126 of side 106, and a proximal edge 128 of side 108. It will be understood that this preferred configuration provides additional space for spine 60 without resecting additional bone.

The manner in which the femoral component 12 may be mounted on the distal end of a femur is well known and need not be described in detail for those skilled in the art.

In operation, the anterior femoral cam 100 and posterior femoral cam 102 of the femoral component 12 articulates with the spine 60 on the tibial bearing 20 to provide posterior stability. Stated alternatively, the spine 60 articulates with anterior femoral cam 100 and posterior femoral cam 102 of femur component 12 to provide stability. In the fully extended position of FIG. 7, the anterior tibial cam 66 of spine 60 engages with the anterior femoral cam 100 to provide, for example, a 3° hyperextension stop. The posterior tibial cam 68 of spine 60 engages posterior femoral cam 102 at about 40° to 60° of flexion, preferably at about 50° of flexion. Normal weight bearing gait involves flexion angles of approximately 40° or less. Thus, for the weight bearing phase of walking, the spine 60 does not engage the posterior femoral cam 102. During activities involving flexion angles greater than about 40° to 60°, such as stair climbing or rising from a chair, the posterior tibial cam 68 of the spine 60 engages the posterior femoral cam 102, providing posterior stability and femoral roll-back, as depicted in FIG. 8. Femoral roll-back is the posterior shift of the tibio-femoral contact point as the knee bends from full extension (FIG. 7) to deep flexion (FIG. 8). As illustrated, the knee system 10 provides for approximately 11 mm of femoral roll-back on a medium sized prosthesis. Preferably, this roll-back, combined with the rotary feature, provides continuous medial and lateral contact between the femoral and tibial bearings surfaces.

Figure 9:
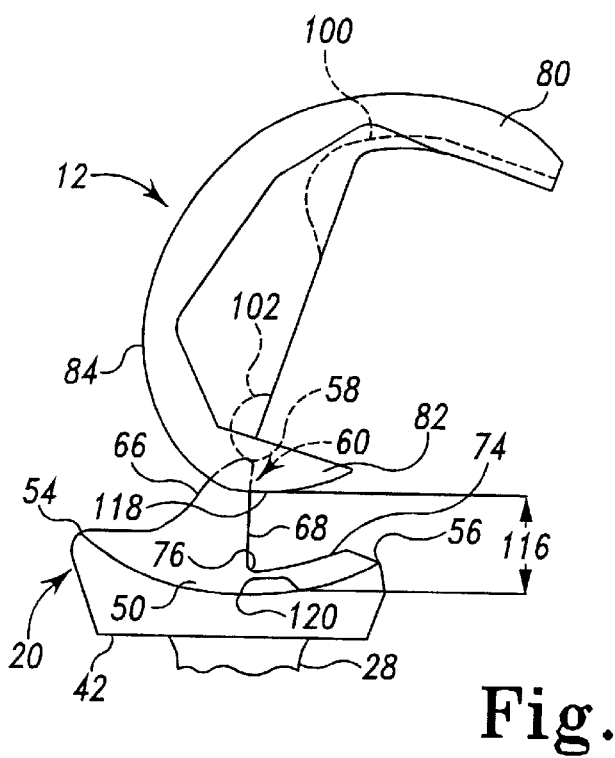
FIG. 9 is a diagrammatical view showing the subluxation height permitted by the system of FIG. 1.

One element considered in the design of the traditional posterior stabilized knees is the subluxation height. This is defined as the distance the femoral component 12 must raise up to sublux or jump over the top of tibial spine 60 during flexion (FIG. 9), the maximum subluxation being indicated at 116. As shown in FIG. 9, maximum subluxation 116 is the distance from a distal-most portion 118 of the femoral component 12 to a corresponding location 120 on bearing surface 50 that femoral component 12 would ordinarily engage at full roll-back. Of course, when the condition depicted in FIG. 9 occurs, dislocation may occur if laxity of collateral ligaments in flexion allows the knee prosthesis to exceed the subluxation height of the design. For example, for a medium sized prosthesis, a subluxation height 116 of 15.4 mm at 90° and 14.5 mm at 120° of flexion (deep flexion is when the dislocation complication occurs) may be suitable. It will be seen that subluxation height 116 is measured from the point indicated at 118 on the condyle bearing 84 to the location 120 on the bearing surface 50.

The surgery techniques for installing the knee system 10 of the present invention may be similar to well known surgical techniques used for installing knees with rotating platform or deep dish bearing components. It will be clear that an exception to this is that the trochlear recessing cut made with the finishing guide for the femur may be cut deeper to provide clearance in the distal femoral bone for the intercondylar notch 88 of the femoral component 12. The larger intercondylar notch 88, in turn, accommodates a taller tibial spine 60, which provides the larger subluxation height.

Although the present invention has been shown and described in detail, the same is by way of example only and not by way of limitation. Numerous changes can be made to the embodiments shown and described without departing from the spirit and scope if the invention. Accordingly, the present invention is to be limited only by the terms of the claims appended hereto.

What is claimed is:

1. A method for providing anterior and posterior stabilization and femoral roll-back to a knee with a knee prosthesis having a rotating tibial bearing, the method comprising the steps of:

attaching a femoral component to the distal end of a femur, the femoral component having condyle surfaces shaped to permit femoral roll-back, the femoral component further having an anterior stabilization mechanism and a posterior stabilization mechanism;

attaching a tibial component to the proximal end of the tibia, the tibial component supporting the tibial bearing which is provided to engage the condyle surfaces; and providing a spine on the tibial bearing which is positioned to cooperate with the anterior stabilization mechanism and the posterior stabilization mechanism, wherein the spine engages the anterior stabilization mechanism at full extension to provide a 3° hyperextension stop.

2. The method of claim 1, in which the spine engages the posterior stabilization mechanism at approximately 50° of flexion and femoral roll-back occurs between 50° and 120° of flexion.

3. The method of claim 2, in which the spine provides a subluxation height of approximately 15 mm at 90° flexion.

4. The method of claim 3, in which the spine also provides a subluxation height of approximately 14 mm at 120° flexion.

5. A knee prosthesis comprising:

a femoral component to be attached to a femur at its distal end and having condyle surfaces spaced apart to define a notch therebetween and having an anterior femoral cam and a posterior femoral cam disposed in the notch; and a tibial component to be attached to a tibia at its proximal end and comprising a platform for attachment to the tibia and a bearing having an anterior portion and a posterior portion, the bearing mounted on the platform for rotational movement about an axis extending generally in the direction of the tibia, wherein the bearing having bearing surfaces for supporting the condyle surfaces and having a spine for extending upwardly into the notch, the spine having an anterior tibial cam for engaging the anterior femoral cam, a posterior tibial cam for engaging the posterior femoral cam, and a peak between the anterior and posterior tibial cams, the anterior tibial cam inclining upwardly from the anterior portion of the bearing and the posterior tibial cam inclining downwardly from the peak at a location adjacent the axis of rotation of the bearing and generally parallel to the axis, and wherein the posterior femoral cam is convexly curved and placed to engage the posterior tibial cam when the knee is at about 40° to 60° of flexion, and the femoral component is shaped to provide femoral roll-back as flexion increases, and wherein the spine and posterior femoral cam are sized and positioned to provide a subluxation height of approximately 15 mm at 90° of flexion.

6. The knee prosthesis of claim 5, in which the tibial bearing comprises ultra high molecular weight polyethyene.

7. A knee prosthesis for implantation in a leg of a patient, the knee prosthesis comprising:

a femoral component to be attached to a femur at its distal end and having a pair of convexly curved condyle surfaces spaced apart to define a notch therebetween, the femoral component further comprising an anterior femoral cam and a posterior femoral cam which extend into the notch; and a tibial component to be attached to a tibia at its proximal end, comprising a platform for attachment to the tibia and a bearing mounted on the platform and rotatable about an axis extending generally in the direction of the tibia;

wherein the bearing having bearing surfaces for supporting the condyle surfaces, and a spine extending superiorly from the platform, the spine positioned and designed to be received in the notch between the anterior and posterior femoral cams, and to engage the anterior femoral cam at approximately full extension and to engage the posterior femoral cam at approximately 40° to 60° of flexion, wherein the spine is of sufficient height to provide a subluxation height of at least 13 mm.

8. The knee prosthesis of claim 7, wherein the spine engages the posterior femoral cam at approximately 50° of flexion.

9. The knee prosthesis of claim 7, in which the pair of condyle surfaces comprise a medial condyle surface and a lateral condyle surface, and the bearing surfaces comprise a medial bearing surface and a lateral bearing surface, and further the condyle surfaces and bearing surfaces are positioned and configured such that the medial condyle surface generally remains in contact with the medial bearing surface and the lateral condyle surface generally remains in contact with the lateral bearing surface from about full extension through about 120° of flexion.

* * * * *